United States Patent [19]

Yen et al.

[11] Patent Number: 5,290,512
[45] Date of Patent: Mar. 1, 1994

[54] METHOD OF DISINFECTING A CONTACT LENS AND PRESERVING A CONTACT LENS CARE SOLUTION

[75] Inventors: Shau F. Yen, Atlanta; Paul C. Nicolson, Dunwoody, both of Ga.

[73] Assignee: Ciba-Geigy Corportion, Ardsley, N.Y.

[21] Appl. No.: 966,770

[22] Filed: Oct. 26, 1992

[51] Int. Cl.$^5$ .................. A01N 25/02; A01N 43/72; A01N 43/80; C11D 3/48
[52] U.S. Cl. ...................................... 422/37; 252/106; 514/839; 514/840
[58] Field of Search ................ 422/37; 514/839, 840; 252/106

[56] References Cited

U.S. PATENT DOCUMENTS

| | | | |
|---|---|---|---|
| 3,761,488 | 9/1973 | Lewis et al. | 260/302 |
| 4,980,176 | 12/1990 | Berke et al. | 514/372 |
| 5,100,905 | 3/1992 | Hsu | 514/372 |
| 5,171,526 | 12/1992 | Wong et al. | 514/840 |

FOREIGN PATENT DOCUMENTS 363011  11/1990  European Pat. Off. ..... A01N 43/80

*Primary Examiner*—Robert J. Warden
*Assistant Examiner*—L. M. Crawford
*Attorney, Agent, or Firm*—Edward McC. Roberts; R. Scott Meece

[57] ABSTRACT

The method of imparting antimicrobial activity to a contact lens composition by adding to the composition an effective amount of 5-chloro-2-methyl-4-isothiazolin-3-one and 2-methyl-4-isothiazolin-3-one.

21 Claims, No Drawings

METHOD OF DISINFECTING A CONTACT LENS AND PRESERVING A CONTACT LENS CARE SOLUTION

The present invention relates to an improved method for imparting antimicrobial activity to contact lens solutions. More particularly, the invention relates to the use of a mixture of 5-chloro-2-methyl-4-isothiazoline-3-one and 2-methyl-4-isothiazoline-3-one for the disinfection of contact lenses and the preservation of contact lens care solutions.

Soft contact lenses are characteristically prepared from hydrophilic polymers, such as polymers of hydroxyethyl methacrylate, crosslinked with a conventional crosslinking agent, such as ethylene glycol dimethacrylate (EDGMA), or more complex copolymer systems including copolymers of HEMA, EDGMA, methacrylic acid and/or poly-N-vinylpyrolidone, and the like. In general, such lenses exhibit marked hydrophilic properties and, when wet, absorb water and are soft and flexible.

An antimicrobial agent used in relation to a contact lens must possess a number of unique characteristics. On one hand, it must be effective against microoorganisms which may be dangerous to the eye. At the same time, it must be tolerated in the delicate ocular environment of the user, and also not damage the contact lens itself. A number of contact lens disinfecting and preserving solutions are known in the art. Typically such solutions employ either sorbic acid, thimerosal, chlorhexidine, a polyquaternary germicide, a synthetic antibiotic or a conventional quaternary germicide, such as benzalkonium chloride. However, these conventional antimicrobial agents have drawbacks that tend to restrict their use. For example, sorbic acid characteristically contains formaldehyde residues, thimerosal in some patients acts as an allergy sensitizer, and chlorhexidine is relatively toxic. Also, a problem exists in that soft contact lens materials have a tendency to bind and concentrate antimicrobial agents and other active ingredients commonly found in contact lens care solutions, in some cases to hazardous levels. For example, benzalkonium chloride is typically not used with soft contact lenses due to its tendency to be taken up into the lens matrix. In addition, many of the antimicrobial agents known to date are relatively ineffective against a number of fungi and yeasts which are problematic in the ocular environment.

Therefore, there exists a need for a method of disinfecting and/or preserving a contact lens or a contact lens care solution which is effective against fungi and yeasts, which is tolerable by the user, and which does not bind with or otherwise damage the contact lens.

SUMMARY OF THE INVENTION

Surprisingly and unexpectedly, it has been found that a mixture of 5-chloro-2-methyl-4-isothiazoline-3-one and 2-methyl-4-isothiazoline-3-one may be used in a method for disinfecting and/or preserving a contact lens or in a contact lens care solution with minimal or none of the above described problems. The mixture has been found to be effective against fungi and yeasts, while also exhibiting low in vitro toxicity and minimal lens uptake.

DETAILED DESCRIPTION OF THE INVENTION

The present invention relates to an improved method for disinfecting and/or preserving contact lenses and contact lens care solutions involving contacting the lens with a composition, typically a solution, having an effective amount of certain substituted 3-isothiazolones comprising 5-chloro-2-methyl-4-isothiazoline-3-one (CAS Registry No. 26172-55-4) and 2-methyl-4-isothiazoline-3-one (CAS Registry No. 2682-20-4). Their structures are as follows:

5-chloro-2-methyl-4-isothiazolin-3-one

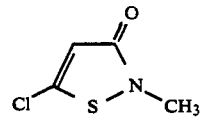

2-methyl-4-isothiazolin-3-one

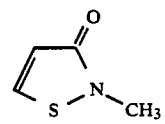

3-isothiazolones are generally described in U.S. Pat. No. 3,761,488 to Lewis et al., which is incorporated herein by reference. The preferred agent used in the present method is composed of a mixture of about 1.15% of 5-chloro-2-methyl-4-isothiazolin-3-one and about 0.35% of 2-methyl-4-isothiazolin-3-one. This agent is available in a product sold under the tradename "Kathon CG," which is available from Rohm and Haas Company, Philadelphia, Pa. The composition of Kathon CG also includes 23.0% Magnesium salts and 75.5% water.

The present invention may, in some cases, be used in conjunction with one or more microbicides to provide a wide range of antimicrobial efficacy. Moreover, surfactants and wetting agents may be provided into the solutions to offer cleaning and wetting features.

The present invention may be employed for preserving a contact lens care solution (such as, for example, a saline solution, a wetting solution, or any other solution coming into contact with the lens) by providing a concentration of approximately 1-300 ppm Kathon in the solution. The amount of the agent for preserving purposes may vary, although it has been found that about 3 ppm is preferred.

The preferred procedure for disinfecting a lens using any one of these solutions is to place the solution having a disinfecting concentration of the mixture into a cup and placing the lens into the solution for four hours. The amount of the agent for disinfecting purposes may vary, although it has been found that about 30 ppm is preferred. The following examples are illustrative of disinfecting solutions which may be used in accordance with the present invention:

EXAMPLE I 11.3 ppm Kathon CG solution 7.8 g sodium chloride
4.76 g disodium hydrogen phosphate
0.714 g sodium phosphate monobasic
0.0086 g 5-chloro-2-methyl-4-isothiazolin-3-one 0.0026 g 2-methyl-4-isothiazolin-3-one
distilled H₂O q.s. 1 liter

EXAMPLE II

50 ppm Kathon CG solution 7.8 g sodium chloride
4.76 g disodium hydrogen phosphate
0.714 g sodium phosphate monobasic
0.0384 g 5-chloro-2-methyl-4-isothiazolin-3-one
0.0117 g 2-methyl-4-isothiazolin-3-one
distilled H₂O q.s. 1 liter

EXAMPLE III

30 ppm Kathon CG solution 6.8 g sodium chloride
4.76 g disodium hydrogen phosphate
0.72 g sodium phosphate monobasic
1.0 g ethylenediamine tetraacid disodium salt
0.0230 g 5-chloro-2-methyl-4-isothiazolin-3-one
0.0070 g 2-methyl-4-isothiazolin-3-one
distilled H₂O q.s 1 liter

EXAMPLE IV

300 ppm Kathon CG solution 6.8 g sodium chloride
4.76 g disodium hydrogen phosphate
0.72 g sodium phosphate monobasic
1.0 g ethylenediamine tetraacid disodium salt
5.0 hydroxyethylcellulose
0.230 g 5-chloro-2-methyl-4-isothiazolin-3-one
0.070 g 2-methyl-4-isothiazolin-3-one
distilled H₂O q.s. 1 liter

EXAMPLE V

7.6 ppm Kathon CG solution 7.3 g sodium chloride
0.91 g disodium hydrogen phosphate
0.12 g potassium phosphate
1.6 g potassium chloride
0.0058 g 5-chloro-2-methyl-4-isothiazolin-3-one
0.0018 g 2-methyl-4-isothiazolin-3-one
distilled H₂O q.s. 1 liter

EXAMPLE VI

15 ppm Kathon CG solution 7.3 g sodium chloride
0.91 g disodium hydrogen phosphate
0.12 g potassium phosphate
1.6 g potassium chloride
0.012 g 5-chloro-2-methyl-4-isothiazolin-3-one
0.0035 g 2-methyl-4-isothiazolin-3-one
distilled H₂O q.s. 1 liter

UPTAKE STUDIES

A study of disinfectant/preservative uptake of solutions according to Examples I and II, as well as other known disinfectant/preservative solutions, was performed. A tetrafilcon A (43% H₂O) contact lens and 5 ml of solution according to Example I was placed in a glass vial. The vial was then incubated at room temperature for 4 hours, after which the concentration of disinfectant/preservative in the solution was determined spectrophotometrically. The percentage of uptake was calculated according to the following:

$$\% \text{ uptake} = \frac{A_c - A_t}{A_c} \times 100\%$$

wherein
$A_c$=the absorption of the disinfectant/preservative solution without lens at 276 nm; and
$A_t$=the absorption of the disinfectant/preservative solution with the lens ay 276 nm.

The tetrafilcon A lens had less than 2.0% uptake of the Kathon CG (5-chloro-2-methyl-4-isothiazolin-3-one and 2-methyl-4-isothiazolin-3-one).

The above procedure was repeated using a fresh Tetrafilcon A lens incubated for 7 days, as well as a number of different type lenses incubated for 4 hour and 7 day periods. Table I below details the results of the study, which clearly show that the method of the present invention results in significantly less lens uptake than benzalkonium chloride and chlorohexidine.

TABLE I

| Solution | Group I (%) 4 hr/7 day | Group II (%) 4 hr/7 day | Group III (%) 4 hr/7 day | Group IV (%) 4 hr/7 day |
|---|---|---|---|---|
| Example 1 | <1.0/<1.0 | <1.0/<1.0 | <2.0/<3.0 | <1.0/<2.0 |
| Example 2 | <1.5/<3.0 | <1.5/<1.5 | <1.5/<1.5 | <1.5/<1.5 |
| 50 ppm BAK | 27/80 | 25/67 | 25/75 | 25/58 |
| 25 ppm chlorohexidine | 35/82 | 27/45 | 34/82 | 30/73 |
| 50 ppm chlorohexidine | 35/80 | 26/44 | 32/82 | 35/74 |

ANTIMICROBIAL EFFICACY STUDY

The results of a study described below shows that the present invention can provide disinfection level microbiological performance in a soft contact lens solution, particularly against key fungal microorganisms such as *C. albicans* and *Aspergillus* ssp. Experiments were conducted using a time course survival/reduction design involving various soaking periods with challenge organisms followed by standard plate count evaluation to characterize antimicrobial efficacy. In the experiments, disinfection panel bacteria and various fungi were used as challenge organisms (See Table II). Microbial survival was tested with exposure times of 4 hours, 24 hours and 7 days (fungi only).

TABLE II

Challenge Microorganisms and Experimental Conditions

| Test Microbe | ATCC # | Plating/Incubation | |
|---|---|---|---|
| *Pseudomonas aeruginosa* | 15442 | TSA | 35° C. |
| *Serratia marcescens* | 14041 | TSA | 35° C. |
| *Staphylococcus epidermidis* | 17917 | TSA | 35° C. |
| *Candida albicans* | 10231 | SDA | 25° C. |
| *Aspergillus fumigatus* | 10894 | SDA | 25° C. |
| *Aspergillus niger* | 16404 | SDA | 25° C. |
| *Fusarium oxysporum* | 26225 | SDA | 25° C. |
| *Cladosporium cladsporioides* | 26688 | SDA | 25° C. |

Test solutions consisted of various concentrations of the antimicrobial active agent in a phosphate buffered saline—5, 7.5, 15, 30 and 50 ppm Kathon CG.

Phosphate buffered saline (PBS) was used as the control for determination of initial inoculums. Prior to testing, all solutions were filtered through a 0.2 um cellulose nitrate membrane to ensure sterility. Tables III through X show the results of the study.

TABLE III

| Test Solution [Kathon CG] | Test Microbe | Initial Inoculum | Exposure Time- CFU/mL, [Log Drop] 4 hour | 24 hour |
|---|---|---|---|---|
| 5 ppm | P. aeruginosa | $1.2 \times 10^4$ | $6.1 \times 10^4$ [1.3] | <10 [TK] |
| 7.5 ppm | | | $4.0 \times 10^4$ [1.5] | <10 [TK] |
| 15 ppm | | | $5.0 \times 10^4$ [1.4] | <10 [TK] |
| 30 ppm | | | $8.2 \times 10^4$ [1.2] | <10 [TK] |
| 50 ppm | | | $9.0 \times 10^5$ [1.1] | <10 [TK] |

TABLE IV

| Test Solution [Kathon CG] | Test Microbe | Initial Inoculum | Exposure Time- CFU/mL, [Log Drop] 4 hour | 24 hour |
|---|---|---|---|---|
| 5 ppm | S. epidermidis | $5.0 \times 10^5$ | $4.1 \times 10^5$ [NK] | $7.4 \times 10^3$ [1.8] |
| 7.5 ppm | | | $3.7 \times 10^5$ [NK] | $9.4 \times 10^3$ [1.7] |
| 15 ppm | | | $3.8 \times 10^5$ [NK] | $1.0 \times 10^4$ [1.7] |
| 30 ppm | | | $\geq 10^5$ [NK] | $1.8 \times 10^4$ [1.4] |
| 50 ppm | | | $\geq 10^5$ [NK] | $1.7 \times 10^4$ [1.5] |

TABLE V

| Test Solution [Kathon CG] | Test Microbe | Initial Inoculum | Exposure Time- CFU/mL, [Log Drop] 4 hour | 24 hour |
|---|---|---|---|---|
| 5 ppm | S. marcescens | $1.2 \times 10^4$ | $5.9 \times 10^5$ [NK] | <10 [TK] |
| 7.5 ppm | | | $5.8 \times 10^5$ [NK] | $1.0 \times 10^1$ [5.1] |
| 15 ppm | | | $5.8 \times 10^5$ [NK] | $1.5 \times 10^1$ [4.9] |
| 30 ppm | | | $\geq 10^5$ [NK] | $2.3 \times 10^1$ [4.7] |
| 50 ppm | (541-25-5) | | $\geq 10^5$ [NK] | $8.7 \times 10^2$ [3.1] |

TABLE VI

| Test Solution [Kathon CG] | Test Microbe | Initial Inoculum | Exposure Time- CFU/mL, [Log Drop] 4 hour | 24 hour | 7 days |
|---|---|---|---|---|---|
| 5 ppm | C. albicans | $2.2 \times 10^6$ | $<1 \times 10^1$ [TK] | $<1 \times 10^1$ [TK] | $<1 \times 10^1$ [TK] |
| 7.5 ppm | | | $<1 \times 10^1$ [TK] | $<1 \times 10^1$ [TK] | $<1 \times 10^1$ [TK] |
| 15 ppm | | | $<1 \times 10^1$ [TK] | $<1 \times 10^1$ [TK] | $<1 \times 10^1$ [TK] |
| 30 ppm | | | $<1 \times 10^1$ [TK] | $<1 \times 10^1$ [TK] | $<1 \times 10^1$ [TK] |
| 50 ppm | | | $<1 \times 10^1$ [TK] | $<1 \times 10^1$ [TK] | $<1 \times 10^1$ [NK] |

TABLE VII

| Test Solution [Kathon CG] | Test Microbe | Initial Inoculum | Exposure Time- CFU/mL, [Log Drop] 4 hour | 24 hour | 7 days |
|---|---|---|---|---|---|
| 5 ppm | A. fumigatus | $2.9 \times 10^4$ | $2.0 \times 10^4$ [2.2] | $6.9 \times 10^3$ [2.6] | $6.9 \times 10^3$ [2.6] |
| 7.5 ppm | | | $9.5 \times 10^3$ [2.5] | $2.3 \times 10^3$ [3.1] | $2.7 \times 10^3$ [3.0] |
| 15 ppm | | | $4.0 \times 10^3$ [2.9] | $7.1 \times 10^2$ [3.6] | $<1 \times 10^1$ [TK] |
| 30 ppm | | | $5.7 \times 10^3$ [2.7] | $1.0 \times 10^1$ [5.5] | $<1 \times 10^1$ [TK] |
| 50 ppm | | | $2.1 \times 10^4$ [NK] | $1.4 \times 10^6$ [NK] | $4.3 \times 10^3$ [0.5] |

TABLE VIII

| Test Solution [Kathon CG] | Test Microbe | Initial Inoculum | Exposure Time- CFU/mL, [Log Drop] 4 hour | 24 hour | 7 days |
|---|---|---|---|---|---|
| 5 ppm | A. niger | $1.4 \times 10^6$ | $3.3 \times 10^4$ [1.6] | $4.8 \times 10^3$ [2.5] | $4.1 \times 10^3$ [2.5] |
| 7.5 ppm | | | $1.4 \times 10^4$ [2] | $4.0 \times 10^3$ [2.5] | $7.8 \times 10^1$ [4.2] |
| 15 ppm | | | $6.5 \times 10^3$ [2.3] | $8.2 \times 10^2$ [3.2] | $<1 \times 10^1$ [TK] |
| 30 ppm | | | $1.0 \times 10^4$ [2.1] | $<1 \times 10^1$ [TK] | $<1 \times 10^1$ [TK] |
| 50 ppm | | | $1.3 \times 10^6$ [NK] | $8.2 \times 10^6$ [NK] | $6.8 \times 10^5$ [NK] |

TABLE IX

| Test Solution [Kathon CG] | Test Microbe | Initial Inoculum | Exposure Time- CFU/mL, [Log Drop] | | |
|---|---|---|---|---|---|
| | | | 4 hour | 24 hour | 7 days |
| 5 ppm | C. cladsporioides | $1.0 \times 10^6$ | $1.9 \times 10^5$ [0.7] | $4.7 \times 10^2$ [2.3] | $<1 \times 10^1$ [TK] |
| 7.5 ppm | | | $1.2 \times 10^5$ [0.9] | $5.3 \times 10^2$ [2.3] | $<1 \times 10^1$ [TK] |
| 15 ppm | | | $1.4 \times 10^5$ [0.9] | $6.0 \times 10^2$ [3.2] | $<1 \times 10^1$ [TK] |
| 30 ppm | | | $1.1 \times 10^4$ [2] | $3.8 \times 10^2$ [3.4] | $<1 \times 10^1$ [TK] |
| 50 ppm | | | $7.0 \times 10^3$ [2.2] | $2.5 \times 10^2$ [3.6] | $<1 \times 10^1$ [TK] |

TABLE X

| Test Solution [Kathon CG] | Test Microbe | Initial Inoculum | Exposure Time- CFU/mL, [Log Drop] | | |
|---|---|---|---|---|---|
| | | | 4 hour | 24 hour | 7 days |
| 5 ppm | F. oxysporum | $7.1 \times 10^5$ | $2.5 \times 10^1$ [5.5] | $<1 \times 10^1$ [TK] | $<1 \times 10^1$ [TK] |
| 7.5 ppm | | | $1.8 \times 10^2$ [4.6] | $<1 \times 10^1$ [TK] | $<1 \times 10^1$ [TK] |
| 15 ppm | | | $9.8 \times 10^1$ [4.9] | $<1 \times 10^1$ [TK] | $<1 \times 10^1$ [TK] |
| 30 ppm | | | $7.5 \times 10^0$ [TK] | $<1 \times 10^1$ [TK] | $<1 \times 10^1$ [TK] |
| 50 ppm | | | $<1 \times 10^1$ [TK] | $<1 \times 10^1$ [TK] | $<1 \times 10^1$ [NK] |

CYTOTOXICITY STUDY

Cell biology experiments were conducted using L929 agar overlay diffusion and SIRC direct contact morphological toxicity assays in order to characterize in vitro cytotoxicity for Kathon CG at 5 to 50 ppm in PBS. L929 agar diffusion experiments showed no significant cytotoxicity for solutions up to 15 ppm; the 30 and 50 ppm solutions caused only mild cytotoxic responses. Evaluation of lenses following 72 hour exposure to the Kathon CG solutions showed no evidence of lens preservative uptake/cytotoxicity. Similarly, SIRC morphology studies demonstrate only mild to moderate cellular effects for Kathon CG under direct contact conditions with limited concentration dependence (e.g. For 30 minutes exposure, Reactivity=2 for 5 ppm and Reactivity=3 for 7.5 to 50 ppm). Overall results, summarized in Tables XI and XII below, indicate low in vitro cytotoxicity for Kathon CG at proposed usage concentrations.

According to the Agar Diffusion Test (as defined in the USP method), a culture shall be deemed to show a cytotoxic effect if microscopic examination reveals malformation, degeneration, sloughing, or lysis of cells within the affected zone, or a moderate to severe reduction in cell layer density. As set forth on the following scale, a Biological Reactivity Grade above 2 indicates significant cytotoxic response under experimental conditions.

| Grade | Reactivity | Description of Reactivity Zone |
|---|---|---|
| 0 | None | No detectable zone around or under sample |
| 1 | Slight | Zone limited to area under the sample |
| 2 | Mild | Zone extends <0.5 cm beyond sample |
| 3 | Moderate | Zone extends 0.5 to 1.0 cm beyond sample |
| 4 | Severe | Zone extends >1.0 cm beyond the sample |

TABLE XI

Evaluation of Kathon CG Solutions using the L929 Agar Overlay Diffusion Assay

| Test Sample | Zone of Lysis | | | | Reactivity |
|---|---|---|---|---|---|
| [Kathon CG] | | | | | |
| 5 ppm | 0.0 | 0.0 | 0.0 | 0.0 | 0 |
| 7.5 ppm | 0.0 | 0.0 | 0.0 | 0.0 | 0 |
| 15 ppm | 0.0 | 0.0 | 0.0 | 0.0 | 0 |
| 30 ppm | 0.2 | 0.2 | 0.1 | 0.2 | 2 |
| 50 ppm | 0.3 | 0.2 | 0.3 | 0.2 | 2 |
| Controls | | | | | |
| 100 ppm BAK | 0.7 | 0.7 | 0.8 | | 3 |
| PBS | 0.0 | 0.0 | 0.0 | | 0 |

TABLE XII

Evaluation of Lenses Following 72 Hour Exposure to Kathon CG Solutions using the L929 Agar Overlay Diffusion Assay

| Test Sample | Zone of Lysis | | | | Reactivity |
|---|---|---|---|---|---|
| [Kathon CG] | | | | | |
| 5 ppm | 0.0 | 0.0 | 0.0 | 0.0 | 0 |
| 7.5 ppm | 0.0 | 0.0 | 0.0 | 0.0 | 0 |
| 15 ppm | 0.0 | 0.0 | 0.0 | 0.0 | 0 |
| 30 ppm | 0.0 | 0.0 | 0.0 | 0.0 | 0 |
| 50 ppm | 0.1 | 0.0 | 0.0 | 0.1 | 0 |
| Controls | | | | | |
| 100 ppm BAK | 0.7 | 0.9 | | | 3 |
| PBS | 0.0 | 0.0 | | | 0 |

Direct Contact SIRC Morphological Toxicity was studied based on Direct Contact USP method. Cytotoxic response is qualitatively measured using a 1-5 grading scale. The following morphological grading system allows estimation of the percentage of cells adversely affected by a given test solution and comparative evaluation of solution cytotoxicity.

| MORPHOLOGICAL TOXICITY GRADING SYSTEM | |
|---|---|
| Grade | Membrane Damage/Cytotoxicity |
| 1 | <10% |
| 2 | <30% |
| 3 | <60% |
| 4 | <80% |
| 5 | <100% |

A culture is judged to show a cytotoxic effect if microscopic examination reveals malformation, degeneration, sloughing, or lysis or cells. A morphological toxicity grade above 2 indicates significant adverse cellular response under direct exposure conditions. The results are set forth as follows:

TABLE XIII

Evaluation of Kathon CG Solutions using the Direct Contact SIRC Morphological Toxicity Assay

| Test Sample | Toxicity Grades | | |
|---|---|---|---|
| | 10 Min | 30 Min | 90 Min |
| [Kathon CG] | | | |
| 5 ppm | 1 1 1 1 | 2 2 2 2 | 3 3 3 3 |
| 7.5 ppm | 1 1 2 1 | 3 3 3 2 | 4 4 4 4 |
| 15 ppm | 2 2 2 2 | 3 3 3 3 | 4 4 4 5 |
| 30 ppm | 2 2 2 2 | 3 3 3 3 | 4 4 4 4 |
| 50 ppm | 2 2 2 2 | 3 3 3 3 | 4 4 4 5 |
| Controls | | | |
| 100 ppm BAK | 5 5 5 5 | 5 5 5 5 | 5 5 5 5 |
| 10 ppm BAK | 2 2 2 2 | 3 3 3 3 | 4 5 5 5 |
| PBS | 1 1 1 1 | 1 1 1 1 | 1 1 1 1 |

What is claimed is:

1. A method for disinfecting a contact lens comprising contacting a hydrophilic contact lens with a composition having an effective disinfecting amount of an agent having 5-chloro-2-methyl-4-isothiazolin-3-one and 2-methyl-4-isothiazolin-3-one.

2. The method of claim 1, wherein said agent comprises approximately 1.15% of 5-chloro-2-methyl-4-isothiazolin-3-one and approximately 0.35% 2-methyl-4-isothiazolin-3-one.

3. The method of claim 1, wherein said composition comprises from about 1 ppm to about 300 ppm of said agent.

4. The method of claim 1, wherein said composition comprises about 30 ppm of said agent.

5. The method of claim 1, wherein said agent is Kathon.

6. A method of preserving a contact lens care composition comprising adding to a contact lens care composition an effective preserving amount of an agent having 5-chloro-2-methyl-4-isothiazolin-3-one and 2-methyl-4-isothiazolin-3-one.

7. The method of claim 6, wherein said agent comprises approximately 1.15% of 5-chloro-2-methyl-4-isothiazolin-3-one and approximately 0.35% 2-methyl-4-isothiazolin-3-one.

8. The method of claim 6, wherein said composition comprises from about 1 ppm to about 300 ppm of said agent.

9. The method of claim 6, wherein said composition comprises about 3 ppm of said agent.

10. The method of claim 6, wherein said contact lens care solution is for use with a hydrophilic contact lens.

11. The method of claim 6, wherein said agent is "Kathon".

12. A composition for disinfecting a hydrophilic contact lens comprising an ophthalmologically acceptable, liquid aqueous medium and, included therein, an effective disinfecting amount of an agent having 5-chloro-2-methyl-4-isothiazolin-3-one and 2-methyl-4-isothiazolin-3-one.

13. The composition of claim 12, wherein said agent comprises approximately 1.15% of 5-chloro-2-methyl-4-isothiazolin-3-one and approximately 0.35% 2-methyl-4-isothiazolin-3-one.

14. The composition of claim 12, wherein said composition comprises from about 1 ppm to about 300 ppm of said agent.

15. The composition of claim 12, wherein said composition comprises about 30 ppm of said agent.

16. The composition of claim 12, wherein said agent is "Kathon".

17. A preserved composition comprising an ophthalmologically acceptable, liquid aqueous medium and, included therein, an effective preserving amount of an agent having 5-chloro-2-methyl-4-isothiazolin-3-one and 2-methyl-4-isothiazolin-3-one.

18. The composition of claim 17, wherein said agent comprises approximately 1.15% of 5-chloro-2-methyl-4-isothiazolin-3-one and approximately 0.35% 2-methyl-4-isothiazolin-3-one.

19. The composition of claim 17, wherein said composition comprises from about 1 ppm to about 300 ppm of said agent.

20. The composition of claim 17, wherein said composition comprises about 3 ppm of said agent.

21. The composition of claim 17, wherein said agent is "Kathon".

* * * * *